United States Patent [19]

Holtkamp, Sr.

[11] Patent Number: Plant 6,110

[45] Date of Patent: Feb. 16, 1988

[54] AFRICAN VIOLET NAMED LITTLE ROSE QUARTZ

[75] Inventor: Reinhold Holtkamp, Sr., Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 823,517

[22] Filed: Jan. 28, 1986

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

An African violet plant named Little Rose Quartz having miniature size and growth habit; strong upright stem carrying light pink semi-double flowers; profuse flowering; continuous flowering, and long-lasting, non-dropping flowers.

1 Drawing Figure

The present invention comprises a new and distinct cultivar of African violet plant, botanically known as *Saintpaulia ionantha*, and hereinafter referred to by the cultivar name Little Rose Quartz.

The new cultivar was originated from a cross made in a controlled breeding program in Isselburg, West Germany and given the breeding number H540/Super Mini. The female, or seed parent was a cultivar designated Saintpaulia Schumensis. The male, or pollen parent was a cultivar designated Z41/S Mini Pink. The objective of the breeding program was to develop a miniature cultivar having certain desired characteristics.

Little Rose Quartz was discovered and selected by me in 1982 as a flowering plant within the progeny of the stated cross in a controlled environment in Isselburg, West Germany. Asexual reproduction of the new cultivar by leaf cuttings, as performed by me at Isselburg, West Germany, has demonstrated that the combination of characteristics as herein disclosed for the new cultivar are firmly fixed and retained through successive generations of asexual reproduction.

Little Rose Quartz has not been observed under all possible environmental conditions. The phenotype may vary significantly with variations in environment such as temperature, light intensity and day length. The following observations, measurements and values describe the new cultivar as grown in Isselburg, West Germany and Nashville, Tenn. under greenhouse conditions which closely approximate those generally used in commercial practice.

The following traits have been repeatedly observed and are determined to be basic characteristics of Little Rose Quartz, which in combination distinguish this African violet as a new and distinct cultivar:

1. The cultivar is miniature and will not grow larger than 6 cm. tall.
2. Strong wirelike upright flower stems curving toward the center.
3. First flash of flowers form a nice bouquet above the leaves.
4. Profuse flowering with the flowers being light pink.
5. Each plant carries up to 8 and more upright flower stems, each of which carries 5 and more flowers..

6. Continuous blooming; flowers are long lasting and do not drop off after maturity, but rather dry off and remain on the peduncle.
7. Plant saleable 10 to 11 weeks after planting of unrooted shoot.
8. Medium green velvet leaves, slightly hairy.
9. Most flowers have additional petals out of the center which give the flowers the appearance of a semi-double.
10. Center of the flower is more intense in color.
11. Seed capsule pushed slightly through.
12. Pointed (spear-shaped) leaves 1.5 to 2.0 cm. in length.

The accompanying photographic drawing shows a typical specimen plant of the new cultivar grown in a 4 cm. pot. The colors appearing in the photograph are as true as possible with color illustrations of this type. The ruler to the right of the plant is in centimeters, highlighting the miniature size and growth habit of Little Rose Quartz.

In the following description, color references are made to The Royal Horticultural Society Colour Chart (R.H.S.), except where general colors of ordinary significance are referred to. Color values were taken under natural light conditions at approximately 1:00 p.m. in Nashville, Tenn. Under coolor growing conditions or more intensive lighting, the pink flower color will be more intense.

Botanical classification: *Saintpaulia ionantha*, Ramat., cv. Little Rose Quartz.

Parentage:

*Male parent.*—Z41/S Mini Pink.

*Female parent.*—Saintpaulia Schumensis.

PROPAGATION

The new cultivar holds its distinguishing characteristics through successive propagations by leaf cuttings.

PLANT

From 5 cm. to 6 cm. tall when grown in pots, and approximately 8–10 cm. in diameter when fully grown.

Leaves:

*Shape.*—Heart-shaped.

*Diameter.*—23 mm. wide and 26 mm. long.

*Texture.*—Leatherlike, slightly hairy.

*Ribs and veins.*—Under side, well pronounced, light green and shiny; light green between the veins.

*Color (upper side).*—147A-B.

*Petioles.*—Strong, wirelike, brownish green, slightly hairy.

Flowers:

*Buds.*—Size: 3–4 mm. before opening. Shape: Bell-shaped. Color: Greenish-brown.

*Sepals.*—Shape: Spear-shaped, hairy; five in number. Color: Greenish-brown.

*Calyx.*—Basifixed.

*Peduncle.*—Character: Strong, wirelike, upright, hairy. Color: Brownish green.

Individual flowers:

*Size.*—18–20 mm. in diameter.

*Shape.*—Semi-double, violet shaped; occasionally single.

*Color (upper side).*—69 between A and B.

*Color (under side).*—69B.

*Borne.*—Each flower stem carries 5 and more flowers on a strong upright peduncle.

Flowering habit: Slightly open flower head, free standing above the leaves; flowers 10 to 11 weeks after planting an unrooted plantlet.

Reproductive organs:

*Stamens.*—Two, well hidden due to flower form.

*Anthers.*—Two, with four anther cells.

*Filaments.*—2 mm., bright green.

*Styles.*—3–4 mm., dark purple with white tip.

Roots: Normally developed, white when young, turning slightly brownish when older.

Disease resistance: Good.

General Observations

Little Rose Quartz in a super miniature violet, which does not grow taller than 6–7 mm. It is clearly a breakthrough in developing miniature violet with the well known Optimara ® characteristics of long-lasting, non-dropping flowers on upright flower stems to form an attractive bouquet free above the leaves. It has continuous blooming characteristics, and under good growing conditions it will not stop blooming. The pink color of the flower intensifies towards the center. The flowers are semi-double and last longer than any violets known to date.

I claim:

1. A new and distinct cultivar of African violet named Little Rose Quartz, as illustrated and described, and particularly characterized by its miniature size and growth habit, strong upright stem carrying light pink semi-double flowers, profuse flowering, continuous flowering and by its long lasting, non-dropping flowers.

* * * * *

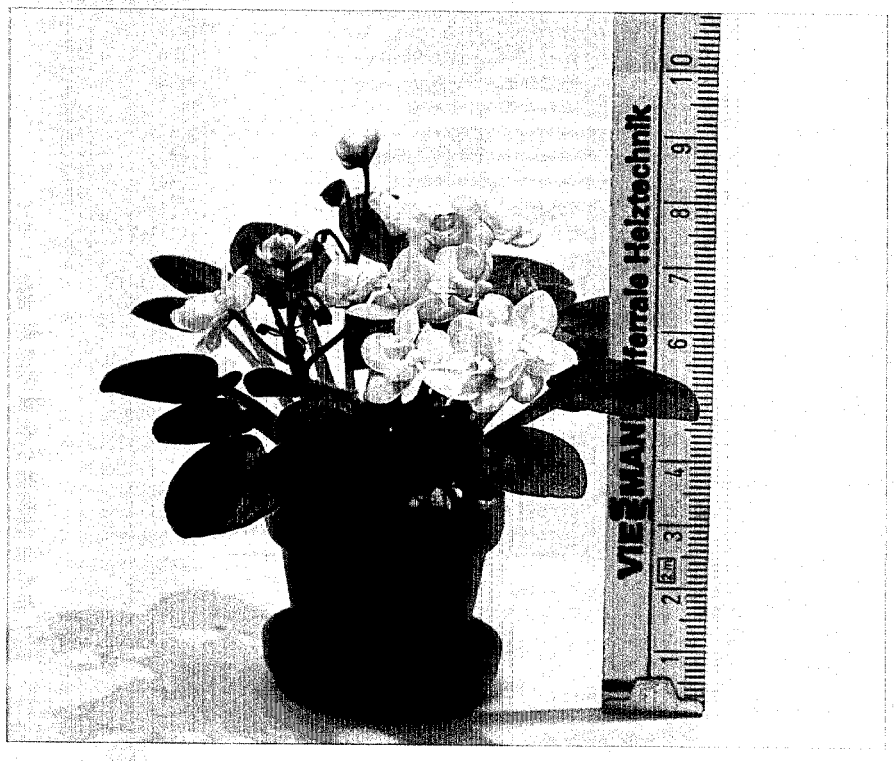
VIESSMANN
Werke
Heiztechnik